United States Patent
Breen et al.

(10) Patent No.: US 6,454,141 B1
(45) Date of Patent: Sep. 24, 2002

(54) NON-PRESSURIZED DRY POWDER DISPENSING APPARATUS

(75) Inventors: Thomas Breen, Coral Springs; Brian Schmitz, Fort Lauderdale, both of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/915,829

(22) Filed: Jul. 25, 2001

(51) Int. Cl.$^7$ ............................................. B65G 53/00
(52) U.S. Cl. ..................... 222/405; 222/168; 222/630; 141/65; 141/130; 406/114; 406/141; 406/145
(58) Field of Search ................................ 222/168, 405, 222/630, 335; 141/65, 130; 406/114, 141, 145

(56) References Cited

U.S. PATENT DOCUMENTS

| | | | |
|---|---|---|---|
| 304,982 A | * 9/1884 | Wiesebrock | ................ 406/114 |
| 3,951,462 A | 4/1976 | De Francisci | |
| 4,265,572 A | * 5/1981 | Bourdois et al. | ............ 406/114 |
| 4,497,598 A | * 2/1985 | Blanton | ...................... 406/114 |
| 4,573,801 A | 3/1986 | Leschonski et al. | |
| 4,859,121 A | * 8/1989 | Deysson et al. | ............ 406/114 |
| 4,895,034 A | 1/1990 | Poole | |
| 5,286,451 A | * 2/1994 | De Silva et al. | ............ 406/114 |
| 5,522,555 A | 6/1996 | Poole | |
| 5,636,921 A | 6/1997 | Murata et al. | |
| 5,816,509 A | * 10/1998 | Ahn et al. | .................. 406/114 |

* cited by examiner

*Primary Examiner*—J. Casimer Jacyna
(74) *Attorney, Agent, or Firm*—Mitchell E. Alter (57) ABSTRACT

An apparatus and a method for dispersing and feeding dry powders without using pressurized air are disclosed. The apparatus comprises a sample holder, a suction probe, a vacuum means and a positional means. The suction probe is positioned above dry powders in the sample holder, a space between the suction probe and the sample holder is substantially small that allows non-pressurized ambient air to form an high velocity downward air flow when a vacuum is applied to the suction probe. A change of air flow direction at an orifice of the suction probe generates a high shear force above the dry powders, which disperses the dry powders into an airstream. The apparatus feeds the dry powder airstream to a particle analyzer with a controlled rate. The apparatus and method are particularly useful in sizing particles using laser diffraction or image analysis techniques.

32 Claims, 5 Drawing Sheets

Dispersed dry powder airstream delivered to a particle analyzer via vacuum

Non-pressurized ambient air enters the space between the suction probe and the sample holder and forms a downward air flow

Vortices created by tapered lower end of the suction probe create particle to wall and particle to particle impacts High shear force generated by a change in air velocity direction Feed rate is controlled by controlling distance from the orifice to the surface of the dry powder

Dry powder

Fig. 4

Velocity direction change over short distance creates high shear force dV/d by 2(V- (-V))/dx = 4V/dx

Fig. 5A

High velocity change over short distance creates high shear force dV/dx by 2(Vmax − Vmin)/dx

Fig. 5B

Fig. 6

NON-PRESSURIZED DRY POWDER DISPENSING APPARATUS

FIELD OF THE INVENTION

The present invention relates to apparatus and methods for dispersing and feeding dry powders, more specifically, to an apparatus and a method of dispersing dry powders into an airstream of particles without using pressurized air, and feeding dry powders for particle analysis with a controlled rate.

BACKGROUND OF THE INVENTION

Dry powders composed of small particles are used and produced in many different industries. Examples of such powders include food, pharmaceuticals, cements, abrasives, pigments, toners, and surface coating materials. It is often very important to measure and control the size of these dry powders as the size can impact the function of a material. An example is the size of pharmaceutical powders which affects the rate at which the drugs are dissolved and absorbed into the body.

There are many methods available for determining the size of particles, including laser diffraction, image analysis and time-of-flight, among others. When measuring the size of dry powders using these methods, problems are often encountered with agglomeration of individual particles into clusters of particles, which results in an incorrect measurement of the particle size. This agglomeration of particles, mainly due to Van der Waals interaction and hydroscopic forces, and various methods to de-agglomerate these clusters are well known in the prior art.

Ideally, a dry powder dispersion and feeding system should create a region of high shear forces, which disperse particle clusters. It can further create wall impacts and particle to particle impacts high enough to disperse clusters of particles, but low enough to prevent "milling", a phenomenon of the individual particle fracturing into smaller particles. For particle sizing measurement, it is also desired to provide the entire sample for a measurement, and to provide the sample at the rate required by the measurement instrument. It is also desirable to restrict the sample powder in the system and to collect the material at the end of the measurement to prevent contamination of the instrument or laboratory environment by potentially hazardous powders.

U.S. Pat. No. 4,573,801 (to Leschonski et al) discloses a method and a dispersing apparatus for producing a gas-solid two phase jet having a constant flow rate and predetermined velocity, therein the solids being fully dispersed. The apparatus has a complex structure comprising a metering groove, a vibrating feeder chute, wiper means for removal of surplus solids, means for compressing the remaining solids, and a flow channel including an injector. In the flow channel the solid particles are accelerated and fully dispersed by the shear force, and the resulting gas-solid particle mixture is discharged as a free jet. Furthermore, before discharge the gas-solid particle mixture is directed several times against impact surfaces to obtain full dispersion. This apparatus uses a groove filling mechanism which is not able to measure the entire sample presented to the instrument.

U.S. Pat. No. 4,895,034 (to Poole) discloses powder dispersing methods and apparatus for use in an aerodynamic particle sizing system utilizing a time-of-flight measurement technique. The apparatus includes a sample container, a device for agitating the powder sample, a separating device, and an air flow for carrying the particles to the outlet. The separating device includes a small annular orifice in which air flow applies high shear forces to clusters of particles to separate them.

U.S. Pat. No. 5,522,555 (to Poole) discloses a dry powder dispersion system. The powder disperser includes a dynamic shear dispersion assembly, and a fluidization assembly, connected by a momentum tube. A pulsed gas jet directed a powder sample in a chamber disperses particles of the powder sample, and the particles are transported into the dynamic shear dispersion assembly, where the particles are accelerated from an impact surface in a rapid acceleration chamber through an annular nozzle. The system controls the dynamic shear force applied to the aerosol transport gas, which affects reaction forces upon the particles within the nozzle.

U.S. Pat. No. 5,636,921 (to Murata et al) discloses a powder dispersing apparatus with a movable powder storing member. The apparatus comprises a pressure vessel, a suction nozzle, a scraper, and a powder storing member inside the pressure vessel, means for rotating and vertically moving the powder storing member. With this apparatus, a flow of air is directed near the sample surface in the powder storing member, and the scraper blade feeds the dry powder sample into the air stream. This feeding mechanism creates an additional surface which must be cleaned between sample measurements to prevent sample and system contamination.

All preceding prior art utilize pressurized air for dispersing dry powders, which brings in several disadvantages. Using pressurized air, in addition to vacuum required in particle sizing instruments, adds cost and complexity to the apparatus. Further, placing the dry powder under pressure raises safety concerns to the operators and working environment. In the event of a failure of the system, dry powders could be "sprayed" into the instrument or the laboratory with potentially damaging results. An example is a pharmaceutical drug being sprayed into the laboratory environment causing injury or illness to the instrument operator. Moreover, It is known in the industry that the jet spraying of dry powders against surfaces causes particle milling, fracturing of the individual particles into smaller particles, when the jet velocities are high. Manufacturers of the particle sizing equipment which utilize the jet spraying methods often instruct the operators to determine the pressure levels where millng of the dry powders begins and maintain pressures below that pressure point. This creates an additional step in the method development and casts doubt on the measured results.

Therefore, it is apparent there exists a special need for a structurally simple, less expensive and environmentally safer dry powder dispensing and feeding apparatus, which meets industrial requirements for particle analysis.

SUMMARY OF THE INVENTION

In one aspect, the present invention relates to a dry powder disperser. The dry powder disperser comprises (a) a sample holder with a closed longitudinal wall, a open top and a closed bottom, (b) a suction probe consisting essentially of (1) an exterior wall with a like shape cross section to a cross section of the sample holder and with a smaller cross section dimension than cross section dimension of the sample holder, and (2) an internal suction channel with an orifice at a bottom of the suction probe, and extended through a top of the exterior wall of the suction probe, and (c) a vacuum means for providing a vacuum in the internal suction channel of the suction probe. When the suction probe is positioned above dry powders in the sample holder, and a vacuum is applied to the internal suction channel, non-pressurized ambient air enters a space between the exterior wall of the suction probe and the longitudinal wall of the sample holder, and forms an high velocity downward air flow along the longitudinal wall of the sample holder, and the downward air flow changing direction at the orifice of the suction probe and generating a high shear force above a surface of the dry powders. The high shear force disperses dry powders, and feeds dispersed dry powders into the internal suction channel.

Figure 1:
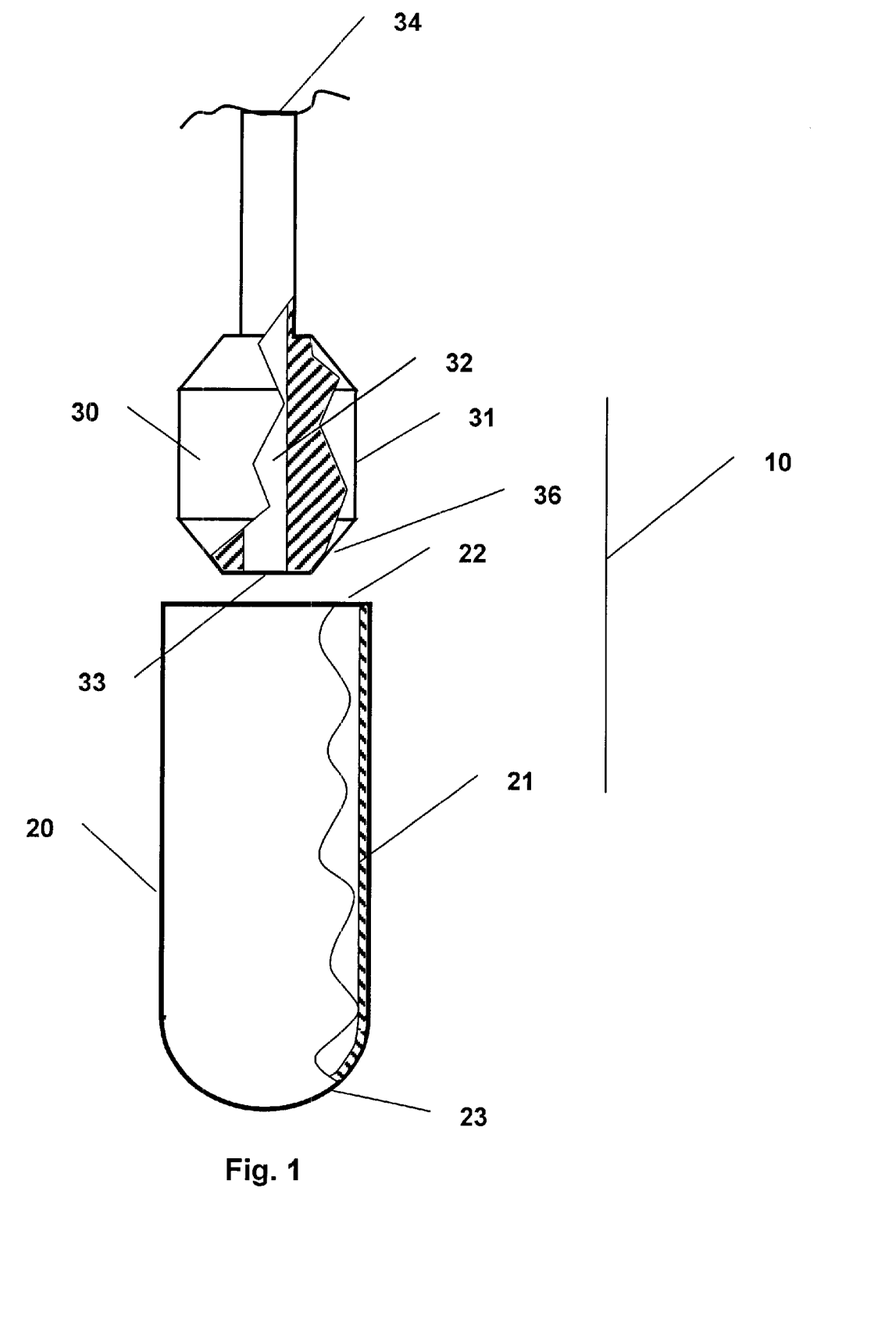
Figure 2:
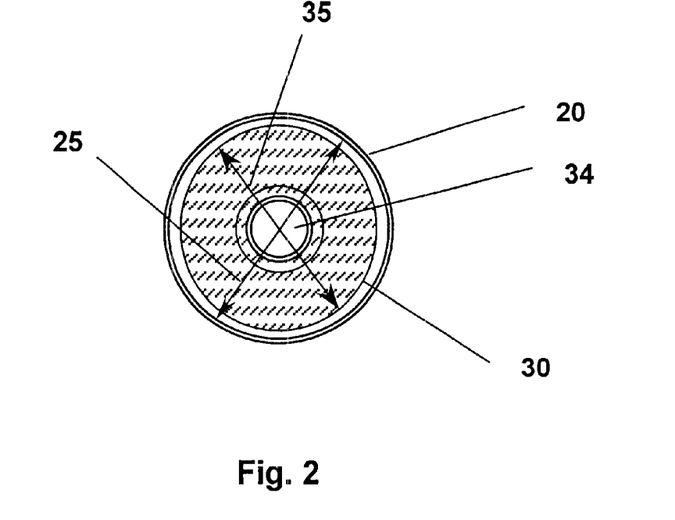
Figure 3:
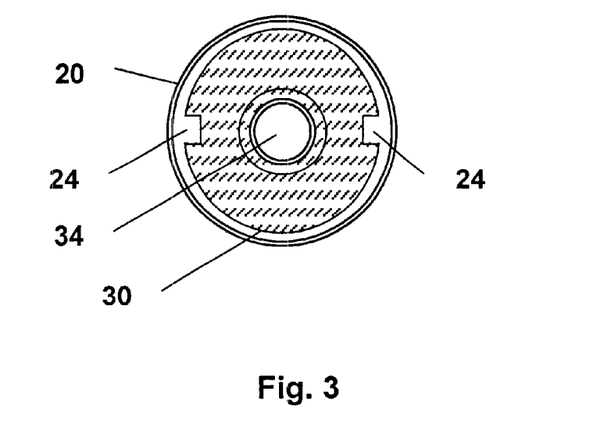
Figure 4:
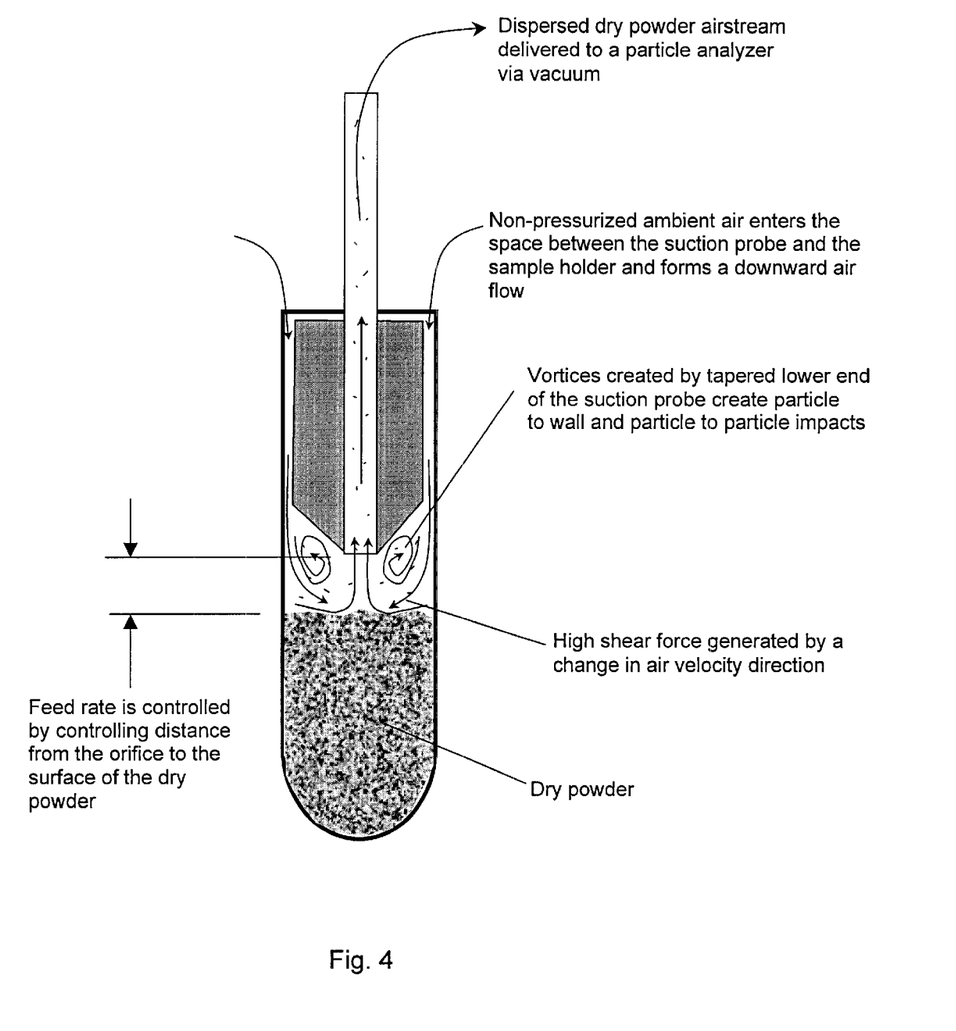
Figure 5A:
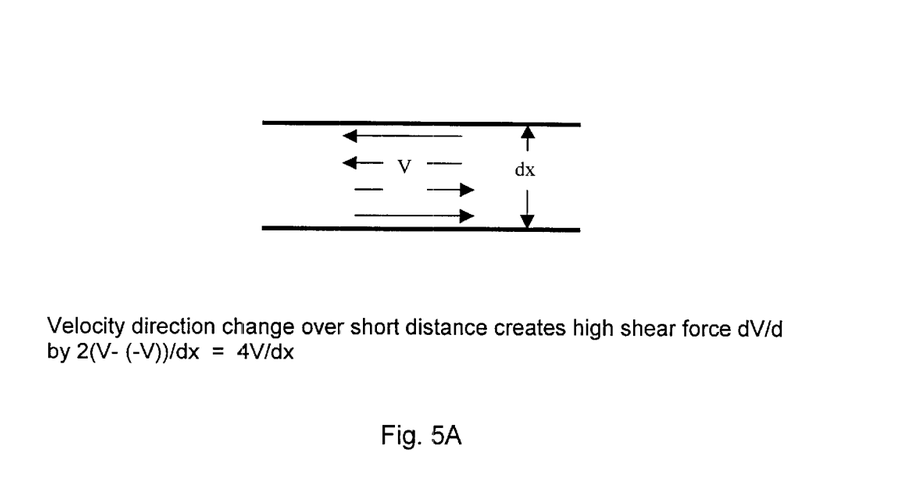
Figure 5B:
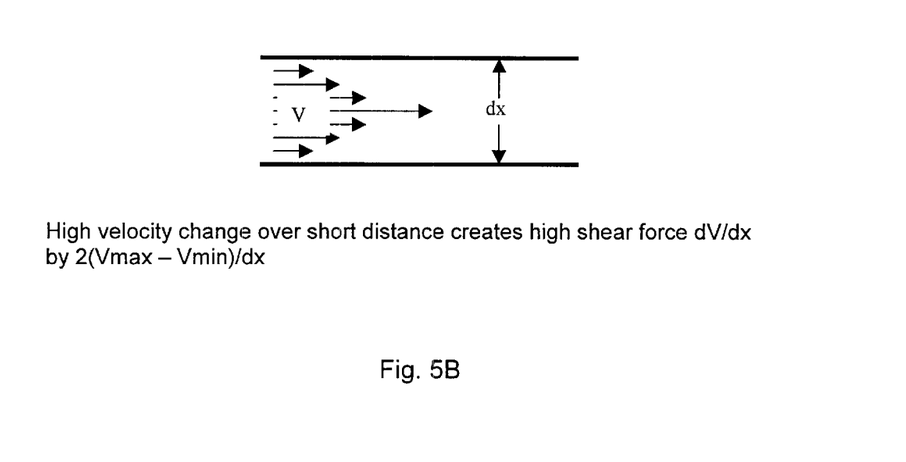

The dry powder disperser has a ratio between a cross s cross sectional area of orifice 33. When a vacuum is applied to internal suction channel 32 from top 34, the vacuum force at orifice 33 drives non-pressurized ambient air entranced from open top 22 of sample holder 20 to form an high velocity downward air flow along the small space between exterior wall 31 of suction probe 30 and longitudinal wall 21 of sample holder 20. At orifice 33, the air flow changes direction from a downward air flow to an upward air flow, as shown in FIG. 4 by the arrows. It is known theoretically that when velocity direction changes over short distance, as illustrated in FIG. 5A, it creates a high shear force. In comparison to a shear force generated by velocity change over a short distance, a situation depicted in FIG. 5B, the principle commonly used in the prior art, to generate an equivalent shear force by velocity direction changes over short distance requires relatively lower velocity. Using this latter mechanism, dry powders can be effectively dispersed without having particles fractured, or "milled", which is known as a side effect of using a high velocity airstream. In sample holder 20, the high shear force generated above the surface of the dry powders disperses dry powders into an airstream of particles, and it further feeds dispersed dry powders into internal suction channel 32 through orifice 33. Through the vacuum line, the dispersed dry powder air stream can be transported to a particle analyzer for a measurement, or a device for particle processing.

In addition to the high shear force, a space formed by tapered low end 36 creates additional vortices above the dry powders. The vortices generate particle to wall impacts, and particle to particle impacts, which further disperse the dry powders.

It is important to control the space between exterior wall 31 of suction probe 30 and longitudinal wall 21 of sample holder 20 to be substantially small, because the space determines the velocity of the downward air flow. Preferably, the cross sectional area of this space is similar to the cross sectional area of orifice 33 of suction probe 30. If the cross sectional area of the space is much smaller than the cross sectional area of orifice 33, the space restricts the downward air flow into the vacuum, which creates higher vacuum pressure levels and lower velocities of the downward air flow. Lower air velocity is detrimental to good dry powder dispersion. If the cross sectional area of the space is much larger than the cross sectional area of orifice 33, the downward air flow also has a lower velocity. It is found that for the purpose of the present invention, the ratio between the cross sectional area of the space between exterior wall 31 of suction probe 30 and longitudinal wall 21 of sample holder 20 and the cross sectional area of orifice 33 is in a range from about 0.9 to about 1.5, and preferably 1.0 to 1.2.

In a suitable working example, orifice 33 of suction probe 3 0.305 inches, which yields a cross sectional area of 0.074 square inches. The inside diameter of sample holder 20 is 1.00 inches, and the outside diameter of suction probe 30 is 0.95 inches. This yields a cross sectional area of the space between exterior wall 31 of suction probe 30 and longitudinal wall 21 of sample holder 20 of 0.074 square inches. In this case, the two cross sectional areas are the same.

In a preferred embodiment, suction probe 30 and sample holder 20 is positioned coaxially, so the distance between exterior wall 31 of suction probe 30 and longitudinal wall 21 of sample holder 20 is equivalent around the periphery.

It has been found that the rate of the dispersed dry powders being fed into orifice 33 is directly dependent on the distance between the surface of the dry powder and orifice 33. The closer this distance is, the faster the feeding rate is. The distance between orifice 33 and the surface of the dry powder can be set depending on the size and density of the dry powder. For a practical application of the present invention, the dry powder dispenser is connected to a particle analyzer, LS 13320 Laser Diffraction Particle Size Analyzer (Beckman Coulter, Inc., Miami, Fla.). The LS 13320 Laser Diffraction Particle Size Analyzer measures a broad range of particles from 0.4 micrometers up to 2000 micrometers in size and any practical density. When analyzing a commercial white baking flour sample of 80 micrometers average diameter and density of approximately 30 lb/ft3, the distance from orifice 33 to the sample surface is approximately 1 inch. When analyzing a sample of glass beads with an average diameter of approximately 1500 micrometers and a density of approximately 160 lb/ft3,the distance from orifice 33 to the sample surface is approximately 0.10 inches.

In a further embodiment of the present invention, a position means is provided to automatically position suction probe 30 relative to sample holder 20, and to the surface of the dry powders. With the position means, the feeding of dispersed dry powders is controlled at a desired rate. Therefore, the dry powder disperser and the position means form an automated apparatus for dispersing and feeding dry powders.

Figure 6:
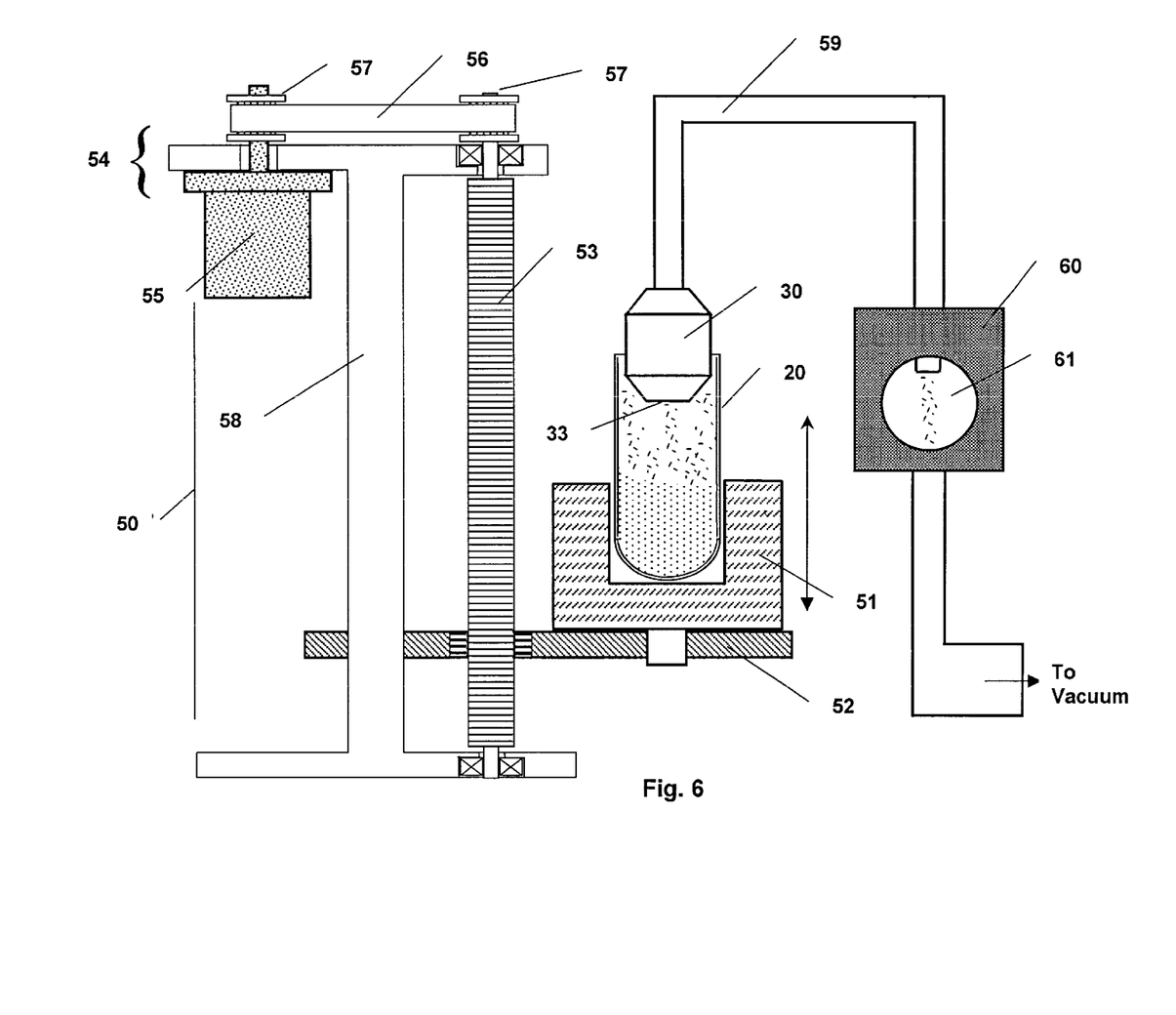

The position means 50, as shown in FIG. 6, comprises a sample holder base 51 supported by a lifting table 52, a lead screw 53 for moving lifting table 52 longitudinally, a driving means 54, a support means 58 for supporting lead screw 53, lifting table 52, and driving means 54, and a control system (not shown). The lifting table 52 is connected to lead screw 53 which drives lifting table 52 longitudinally to adjust the position of sample hold 20 relative to orifice 33. Lead screw 53 is driven by driving means 54 which comprises a stepper motor 55, a timing belt 56 and two timing gears 57. In a preferred embodiment, sample holder base 51 further rotates sample holder 20 with respect to suction probe 30 to facilitate a more uniform feed rate of dry powders.

FIG. 6 also shows an example of using the apparatus for dispersing and feeding dry powders with an optical particle analyzer. As shown, suction probe 30 is connected at top through a hollow tubing 59 to a particle measurement cell 60. The dispersed particles are measured by a laser beam or image capture means through an optically clear measurement window 61.

The control system measures the feeding rate of the dispersed dry powders by a suitable particle measurement known in the art, and controls the position of lifting table 52 which controls the distance between orifice 33 and the surface of dry powders, to achieve a desired particle feeding rate.

In one embodiment, a closed loop control system is used in conjunction with a particle sizing instrument, wherein the particle sizing instrument is not only the designated receiving instrument of the dispersed particles, it also inputs information of a real time particle feeding rate versus the desired feeding rate to the closed loop control system.

When the apparatus for dispersing and feeding dry powders is in operation for a routine particle analysis, sample holder base 51 and suction probe 30 is prealigned. No lateral adjustment is needed for sample holder 20. Sample holder 20 is removable, it is replaced after each sample being analyzed. Lifting table 52 positions sample holder 20 through sample holder base 51 at an initial longitudinal position, where vacuum means is activated to start dispersing and feeding a dry powder sample into the particle sizing instrument. The real time particle feeding rate is measured by the particle sizing instrument, for example by the extinction of the laser beam, and provided to the closed loop control system. A desired extinction value is compared to the real time extinction value, and the difference is used to generate a signal by the control system, which drives lifting table 52 to adjust the distance between orifice 33 and the surface of dry powders to achieve the desired particle feeding rate. With this mechanism, the position means provide a continuous control of the particle feeding rate to the particle analyzer. When the dry powder sample amount reduces upon feeding, position means adjusts continuously the position of sample holder 20 to provide a constant feeding rate. In this manner, entire dry powder sample in sample holder 20 are used for the particle analysis, which is required by the industrial standard for laser diffraction measurements.

The apparatus for dispersing and feeding dry powders can provide a wide range of feeding rate. In the previously described working example for providing dispersed dry powders to LS 13320 Laser Diffraction Particle Size Analyzer, the instant apparatus can provide various feeding rates from about $1 \times 10^5$ cc/s (cubic centimetres per sec) to about 4 cc/s. Furthermore, the feeding rate range can be changed through the system design to accommodate the need of a particle analyzer or a particle processing system.

It is apparent based on above descriptions that the apparatus of present invention have several advantages. The apparatus creates a region of high shear forces that disperses dry powders without use of a pressurized gas. Further, the geometry of the suction probe further creates particle to wall impacts and particle to particle impacts that are high enough to disperse clusters of particles, but low enough to prevent the "milling", fracturing of the individual particles into smaller particles. Moreover, by restricting the sample powder in the system only under negative pressure (vacuum) for both dispersion and feeding into the particle analyzer, the system is "fail-safe" in the event of component failure, as compared to pressurized air systems. Additionally, the apparatus enables the entire sample to be dispersed and fed into a connected particle analyzer, and automatically feeds the dispersed particles at the rate required by the particle analyzer. The apparatus and method of the present invention are particularly useful in sizing particles using laser diffraction or image analysis techniques.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A dry powder disperser comprising:
   (a) a sample holder with a closed longitudinal wall, a open top and a closed bottom,
   (b) a suction probe consisting essentially of (1) an exterior wall with a like shape cross section to a cross section of said sample holder and with a smaller cross section dimension than cross section dimension of said sample holder, and (2) an internal suction channel with an orifice at a bottom of said suction probe, and extended through a top of said exterior wall of said suction probe, and
   (c) a vacuum means for providing a vacuum in said internal suction channel of said suction probe, and
   wherein when said suction probe is positioned above dry powders in said sample holder, and a vacuum is applied to said internal suction channel, non-pressurized ambient air enters a space between said exterior wall of said suction probe and said longitudinal wall of said sample holder, and forms an high velocity downward air flow along said longitudinal wall of said sample holder, and said downward air flow changing direction at said orifice of said suction probe and generating a high shear force above a surface of said dry powders; and wherein said high shear force disperses dry powders, and feeds dispersed dry powders into said internal suction channel and wherein said dry powder disperser is connected with a particle analyzer for providing dispersed dry powders for a particle analysis.

2. The dry powder disperser of claim 1, wherein a ratio between a cross sectional area of said space and a cross sectional area of said orifice is in a range from about 0.9 to about 1.5.

3. The dry powder disperser of claim 2, wherein a ratio between a cross sectional area of said space and a cross sectional area of said orifice is in a range from about 1.0 to about 1.2.

4. The dry powder disperser of claim 1, wherein said exterior wall of said suction probe is tapered at a lower end of said suction probe.

5. The dry powder disperser of claim 4, wherein an additional space formed by said tapered lower end of said suction probe above said surface of claim said dry powders creates air vortices, said vortices further generating a particle to wall and particle to particle impacts.

6. The dry powder disperser of 4, wherein said exterior wall of said suction probe further comprises one or more longitudinal slots for facilitating said downward air flow.

7. The dry powder disperser of claim 1, wherein said cross section of said sample holder is circular.

8. The dry powder disperser of claim 1, wherein said cross section of said suction probe is circular.

9. The dry powder disperser of claim 1, wherein said suction probe is positioned coaxially with said sample holder.

10. The dry powder disperser of claim 1, wherein said internal suction channel of said suction probe is cylindrical.

11. The dry powder disperser of claim 1, wherein said sample holder is removable from said dry powder disperser.

12. An apparatus for dispersing and feeding dry powders comprising:
   (a) a sample holder with a closed longitudinal wall, a open top and a closed bottom,
   (b) a suction probe consisting essentially of (1) an exterior wall with a like shape cross section to a cross section of said sample holder and with a smaller cross section dimension than cross section dimension of said sample holder, and (2) an internal suction channel with an orifice at a bottom of said suction probe, and extended through a top of said exterior wall of said suction probe, and
   (c) a vacuum means for providing a vacuum in said internal suction channel of said suction probe, and
   (d) a positioning means for positioning said suction probe in said sample holder, wherein when a vacuum is applied to said internal suction channel, non-pressurized ambient air enters a space between said exterior wall of said suction probe and said longitudinal wall of said sample holder, and forms an high velocity downward air flow along said longitudinal wall of said sample holder, and said downward air flow changing direction at said orifice of said suction probe and generating a high shear force above a surface of said dry powders; and wherein said high shear force disperses dry powders, and feeds dispersed dry powders into said internal suction channel and wherein said positioning means comprises a sample holder base supported by a lifting table, a lead screw for moving said lifting table longitudinally, a driving means to drive said lead screw, a support means for supporting said lead screw, said driving means, and said lifting table, and a control system.

13. The apparatus of claim 12, wherein said positioning means positions said sample holder longitudinally to control a distance between said orifice of said suction probe and said surface of said dry powders inside said sample holder.

14. The apparatus of claim 12, wherein said positioning means controls a feeding rate of dry powders into said internal suction channel by controlling a distance between said orifice and said surface of said dry powders in said sample holder.

15. The apparatus of claim 12, wherein said positioning means further rotates said sample holder to facilitate a homogeneous feeding of dry powders.

16. The dry powder disperser of claim 12, wherein a ratio between a cross sectional area of said space and a cross sectional area of said orifice is in a range from about 0.9 to about 1.5.

17. The dry powder disperser of claim 16, wherein a ratio between a cross sectional area of said space and a cross sectional area of said orifice is in a range from about 1.0 to about 1.2.

18. The apparatus of claim 12, wherein said exterior wall of said suction probe is tapered at a lower end of said suction probe.

19. The apparatus of claim 18, wherein an additional space formed by said tapered lower end of said suction probe above said surface of said dry powders creates air vortices, said vortices further generating a particle to wall and particle to particle impacts.

20. The apparatus of claim 12, wherein said exterior wall of said suction probe further comprises one or more longitudinal slots for facilitating said downward air flow.

21. The apparatus of claim 12, wherein said cross section of said sample holder is circular.

22. The apparatus of claim 12, wherein said cross section of said suction probe is circular.

23. The apparatus of claim 12, wherein said suction probe is positioned coaxially with said sample holder.

24. The apparatus of claim 12, wherein said internal suction channel of said suction probe is cylindrical.

25. The apparatus of claim 12, wherein said sample holder is removable from said apparatus.

26. The apparatus of claim 12, wherein said vacuum means is connected to a top end of said suction probe.

27. The apparatus of claim 12, wherein said apparatus is connected to a particle analyzer for providing dispersed dry powders for a particle analysis.

28. A method of dispersing dry powders comprising the steps of:
(a) placing a dry powder sample in a sample holder comprising a closed longitudinal wall, a open top and a closed bottom,
(b) positioning a suction probe above said dry powder sample, wherein said suction probe comprises an exterior wall with a like shape cross section to a cross section of said sample holder and with a smaller cross section dimension than cross section dimension of said sample holder, an internal suction channel with an orifice at a bottom of said suction probe, extended through a top of said exterior wall of said suction probe, and said probe being connected to a vacuum means for providing a vacuum in said internal suction channel; and (c) applying vacuum to said suction probe, wherein non-pressurized ambient air enters a space between said exterior wall of said suction probe and said longitudinal wall of said sample holder, and forms an high velocity downward air flow along said longitudinal wall of said sample holder, and said downward air flow changing direction at said orifice of said suction probe and generating a high shear force above a surface of said dry powders; and wherein said high shear force disperses dry powders, and feeds dispersed dry powders into said internal suction channel and wherein said exterior wall of said suction probe is tapered at a lower end of said suction probe, and an additional space formed by said tapered lower end of said suction probe above said surface of said dry powders creates vortices, said vortices further generating a particle to wall and a particle to particle impacts.

29. The dry powder disperser of claim 28, wherein a ratio between a cross sectional area of said space and a cross sectional area of said orifice is in a range from about 0.9 to about 1.5.

30. The dry powder disperser of claim 29, wherein a ratio between a cross sectional area of said space and a cross sectional area of said orifice is in a range from about 1.0 to about 1.2.

31. The method of claim 28 further comprising controlling a feed rate of said dry powders by controlling a distance from said orifice to said surface of said dry powders.

32. The method of claim 28 further comprising feeding dispersed dry powders into a particle analyzer for a particle analysis.

* * * * *